US012711873B2

(12) United States Patent
Lee et al.

(10) Patent No.: US 12,711,873 B2
(45) Date of Patent: Aug. 18, 2026

(54) SURGICAL PROCEDURE LABELING AND TEACHING SYSTEM AND METHOD THEREOF

(71) Applicant: SMART SURGERY, Taipei (TW)

(72) Inventors: Yu-Chieh Lee, Taipei (TW); Yi-Ta Shen, Taipei (TW); Hsin-Man Chiang, Taipei (TW)

(73) Assignee: SMART SURGERY, Taipei City (TW)

(*) Notice: Subject to any disclaimer, the term of this patent is extended or adjusted under 35 U.S.C. 154(b) by 534 days.

(21) Appl. No.: 17/673,748

(22) Filed: Feb. 16, 2022

(65) Prior Publication Data

US 2023/0260413 A1 Aug. 17, 2023

(51) Int. Cl.

| | |
|---|---|
| ***G09B 5/02*** | (2006.01) |
| ***G06F 3/0482*** | (2013.01) |
| ***G06F 3/0484*** | (2022.01) |
| ***G06T 7/00*** | (2017.01) |
| ***G09B 5/06*** | (2006.01) |
| ***G11B 27/10*** | (2006.01) |
| ***G16H 30/40*** | (2018.01) |
| ***G16H 70/20*** | (2018.01) |

(52) U.S. Cl.

CPC ............. *G09B 5/02* (2013.01); *G06F 3/0482* (2013.01); *G06F 3/0484* (2013.01); *G06T 7/0014* (2013.01); *G09B 5/06* (2013.01); *G11B 27/10* (2013.01); *G16H 30/40* (2018.01); *G16H 70/20* (2018.01); *G06T 2200/24* (2013.01); *G06T 2207/10016* (2013.01); *G06T 2207/20092* (2013.01); *G06T 2207/30004* (2013.01)

(58) Field of Classification Search

CPC ... G09B 5/02; G09B 5/06; G09B 9/00; G09B 23/28–34; G16H 30/00–40

See application file for complete search history.

(56) References Cited

U.S. PATENT DOCUMENTS

| | | | | |
|---|---|---|---|---|
| 2013/0184584 A1* | 7/2013 | Berkey | ................ | A61B 8/5292 600/441 |
| 2016/0180743 A1* | 6/2016 | Ahmad | .................. | G09B 23/28 434/262 |
| 2021/0313077 A1* | 10/2021 | Smurro | .................... | G06N 3/08 |

* cited by examiner

*Primary Examiner* — Kang Hu
*Assistant Examiner* — Correll T French
(74) *Attorney, Agent, or Firm* — Chih Feng Yeh; Yongjean Consulting Inc.

(57) ABSTRACT

A surgical procedure labeling and teaching system and a method thereof are disclosed. When one of names of to-be-labeled surgical images on a surgical image selection area of a user interface is selected, the to-be-labeled surgical image corresponding to the selected name is displayed on a surgical image labeling area of the user interface; after one of surgery label blocks on a surgery label selection area of the user interface is selected, a user can circle a surgery labeling area to establish a surgery feature label on the surgical image labeling area. A teaching interface can map the labeled surgical image to the to-be-labeled surgical image, so as to provide a surgical procedure teaching corresponding to the to-be-labeled surgical image. The technical effect of providing surgical procedure teaching by using the labeling-reference surgical image to assist in labeling and selecting of the to-be-labeled surgical image is achieved.

6 Claims, 11 Drawing Sheets

20

30

Figure 10B:
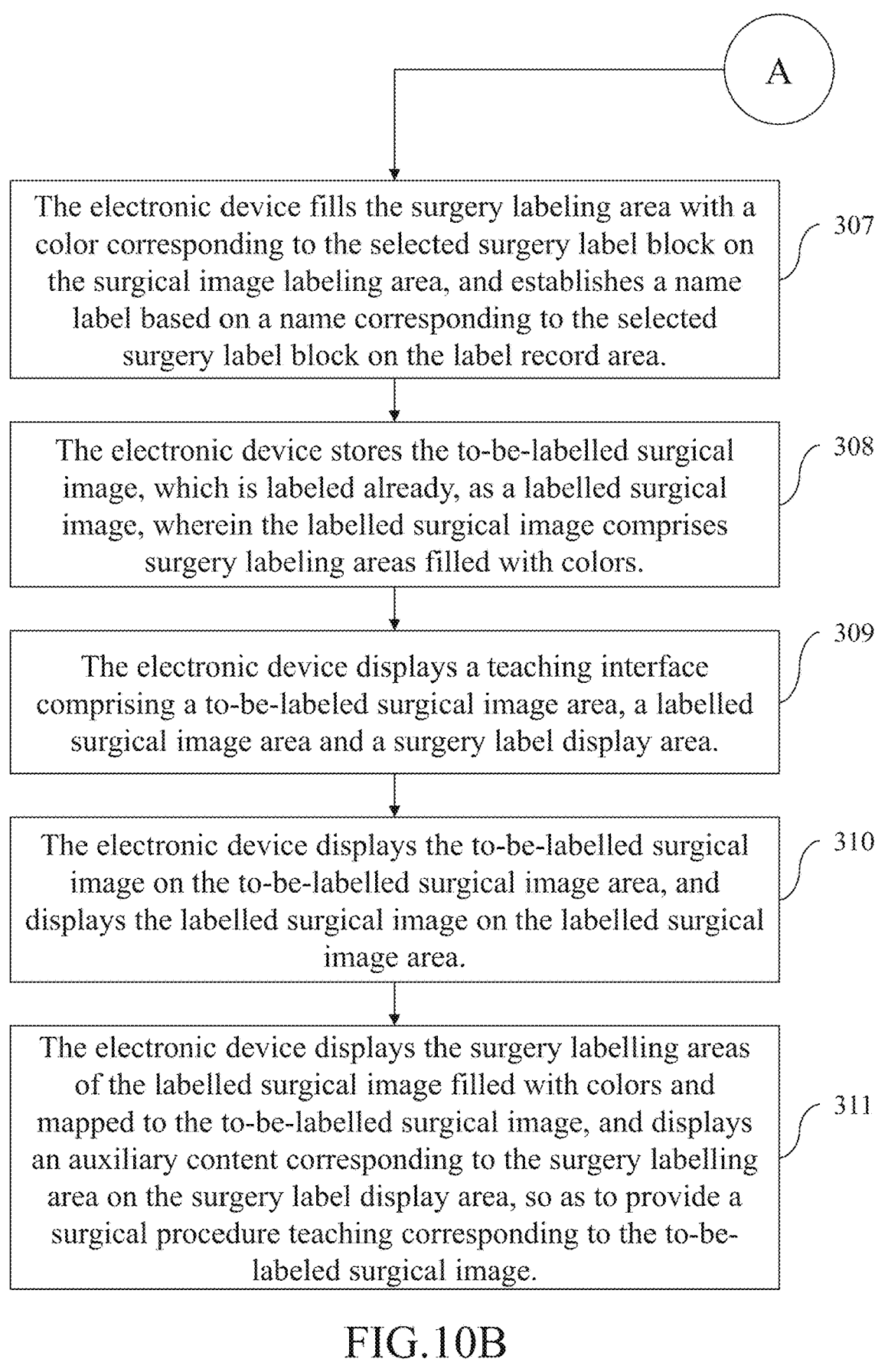

A

The electronic device fills the surgery labeling area with a color corresponding to the selected surgery label block on the surgical image labeling area, and establishes a name label based on a name corresponding to the selected surgery label block on the label record area.

307

The electronic device stores the to-be-labelled surgical image, which is labeled already, as a labelled surgical image, wherein the labelled surgical image comprises surgery labeling areas filled with colors.

308

The electronic device displays a teaching interface comprising a to-be-labeled surgical image area, a labelled surgical image area and a surgery label display area.

309

The electronic device displays the to-be-labelled surgical image on the to-be-labelled surgical image area, and displays the labelled surgical image on the labelled surgical image area.

310

The electronic device displays the surgery labelling areas of the labelled surgical image filled with colors and mapped to the to-be-labelled surgical image, and displays an auxiliary content corresponding to the surgery labelling area on the surgery label display area, so as to provide a surgical procedure teaching corresponding to the to-be-labeled surgical image.

SURGICAL PROCEDURE LABELING AND TEACHING SYSTEM AND METHOD THEREOF

BACKGROUND

1. Technical Field

The present invention is related to a circling and labeling system and a method thereof, and more particularly to a surgical procedure labeling and teaching system providing a labeling-reference surgical image on a user interface to assist in labeling and circling a to-be-labeled surgical image, and a method thereof.

2. Related Art

The dissemination of medical knowledge mostly needs to use videos or images for medical teaching. With the development of medical equipment, surgical videos can be recorded during the process of surgical procedure, and the surgical videos are useful for medical teaching. During the medical teaching with video, the teacher can pause the surgical video and start explaining the video content when the video reaches the key step of the surgical procedure; however, the existing video playback application does not have an auxiliary tool to label the paused video content for medical teaching.

According to above-mentioned contents, what is needed is to develop an improved technical solution to solve the conventional technology problem of lacking an auxiliary tool to label the surgical procedure video for better medical teaching.

SUMMARY

An objective of the invention present is to provide a surgical procedure labeling and teaching system and a method thereof, to solve the problem that the conventional editing operation must frequently switch windows because the conventional image editing tool is unable to display a to-be-edited image and a labeling-reference surgical image in a working window at the same time.

In order to achieve the objective, the present invention provides a surgical procedure labeling and teaching system executed in an electronic device, the electronic device includes a hardware processor is configured to execute following instructions stored in a memory:

Displaying a user interface, wherein the user interface comprises a surgical image selection area, a surgical image labeling area, a label record area, a surgery video playback area, an image-labeling reference area and a surgery label selection area. Playing a surgery video on the surgery video playback area. When one of names of to-be-labelled surgical images on the surgical image selection area is selected, displaying a to-be-labelled surgical image corresponding to the selected name on the surgical image labelling area, and displaying a labelling-reference surgical image corresponding to the selected name on the image-labelling reference area. When one of names of to-be-labelled surgical images on the surgical image selection area is selected, calculating a period from a video time point minus a preset time length to the video time point plus the preset time length based on the video time point of the selected to-be-labeled surgical image, to capture a part of the surgery video in the period to generate and play a captured surgery video. When one of surgery label blocks on the surgery label selection area is selected, receiving multiple connected operating points in the surgical image labelling area to generate newly a surgery labelling area wherein a edge of newly the surgery labelling area is formed by multiple connected operating points, and filling the surgery labeling area with a color corresponding to the selected surgery label block on the surgical image labeling area. When coordinates of at least one of operating points are located within a coordinate range of established the surgery labelling area, a display priority of newly the surgery labelling area is determined higher or lower than previously the surgery labelling area based on the display priority of previously the surgery labelling area, newly the surgery labelling area or previously the surgery labelling area having a high display priority is displayed over newly the surgery labelling area or previously the surgery labelling area having a low display priority. Establishing and displaying a background label on the label record area, wherein after the surgery labelling area is circled on the surgical image labelling area, establishing a name label on the label record area based on a name corresponding to the selected surgery label block. Storing the labelled to-be-labelled surgical image as a labelled surgical image, wherein the labelled surgical image comprises surgery labeling areas filled with colors. Displaying a teaching interface including a to-be-labeled surgical image area, a labelled surgical image area and a surgery label display area, wherein displaying the to-be-labelled surgical images on the to-be-labelled surgical image area, and displaying the labelled surgical image on the labelled surgical image area, and providing a surgical procedure teaching corresponding to the to-be-labeled surgical image by the surgery labelling areas of the labelled surgical image filled with colors and mapped to the to-be-labelled surgical image, and displaying multiple auxiliary content blocks with colors and names corresponding to the surgery labelling areas on the surgery label display area.

In order to achieve the objective, the present invention provides a surgical procedure labeling and teaching method including steps of: displaying a user interface comprising a surgical image selection area, a surgical image labeling area, a label record area, a surgery video playback area, an image-labeling reference area, and a surgery label selection area, by an electronic device; playing a surgery video on the surgery video playback area, by the electronic device; when one of names of to-be-labelled surgical images displayed on the surgical image selection area is selected, displaying a to-be-labelled surgical image corresponding to the selected name on the surgical image labelling area, by the electronic device; when one of the names of the to-be-labelled surgical images displayed on the surgical image selection area is selected, displaying a labelling-reference surgical image corresponding to the selected name on the image-labelling reference area, by the electronic device; when one of names of to-be-labelled surgical images on the surgical image selection area is selected, calculating a period from a video time point minus a preset time length to the video time point plus the preset time length based on the video time point of the selected to-be-labeled surgical image, to capture a part of the surgery video in the period to generate and play a captured surgery video, by the electronic device; establishing and displaying a background label on the label record area, by the electronic device; when one of surgery label blocks displayed on the surgery label selection area is selected, receiving multiple connected operating points in the surgical image labelling area to generate newly a surgery labelling area by the electronic device wherein a edge of newly the surgery labelling area is formed by multiple connected operating points; when coordinates of at least one of operating points are located within a coordinate range of established the surgery labelling area, a display priority of newly the surgery labelling area is determined higher or lower than previously the surgery labelling area based on the display priority of previously the surgery labelling area newly the surgery labelling area or previously the surgery labelling area having a high display priority is displayed over newly the surgery labelling area or previously the surgery labelling area having a low display priority; filling the surgery labeling area with a color corresponding to the selected surgery label block on the surgical image labeling area, and establishing a name label based on a name corresponding to the selected surgery label block on the label record area, by the electronic device; storing the to-be-labelled surgical image, which is labeled already, as a labelled surgical image, by the electronic device, wherein the labelled surgical image comprises surgery labeling areas filled with colors; displaying a teaching interface comprising a to-be-labeled surgical image area, a labelled surgical image area and a surgery label display area, by an electronic device; displaying the to-be-labelled surgical image on the to-be-labelled surgical image area, and displaying the labelled surgical image on the labelled surgical image area, by the electronic device; displaying the surgery labelling areas of the labelled surgical image filled with colors and mapped to the to-be-labelled surgical image, and displaying multiple auxiliary content blocks with colors and names corresponding to the surgery labelling areas on the surgery label display area, by the electronic device, so as to provide a surgical procedure teaching corresponding to the to-be-labeled surgical image.

According to the above-mentioned system and method of the present invention, the difference between the present invention and the conventional technology is that, in the present invention, when one of the names of the to-be-labeled surgical images on the surgical image selection area of the user interface is selected, the to-be-labeled surgical image corresponding to the selected name is displayed on the surgical image labeling area of the user interface, and after one of the surgery label blocks on the surgery label selection area of the user interface is selected, the user can circle the surgery labeling area to establish the surgery feature label on the surgical image labeling area, and the teaching interface can map the labeled surgical image to the to-be-labeled surgical image, so as to provide the surgical procedure teaching corresponding to the to-be-labeled surgical image.

According to the above-mentioned technical solution of the present invention, the technical effect of providing surgical procedure teaching by using the labeling-reference surgical image to assist the labeling and selecting of the to-be-labeled surgical image can be achieved.

BRIEF DESCRIPTION OF THE DRAWINGS

The structure, operating principle and effects of the present invention will be described in detail by way of various embodiments which are illustrated in the accompanying drawings.

FIGS. 10A and 10B are flowcharts of a surgical procedure labeling and teaching method of the present invention.

DETAILED DESCRIPTION

Figure 1:
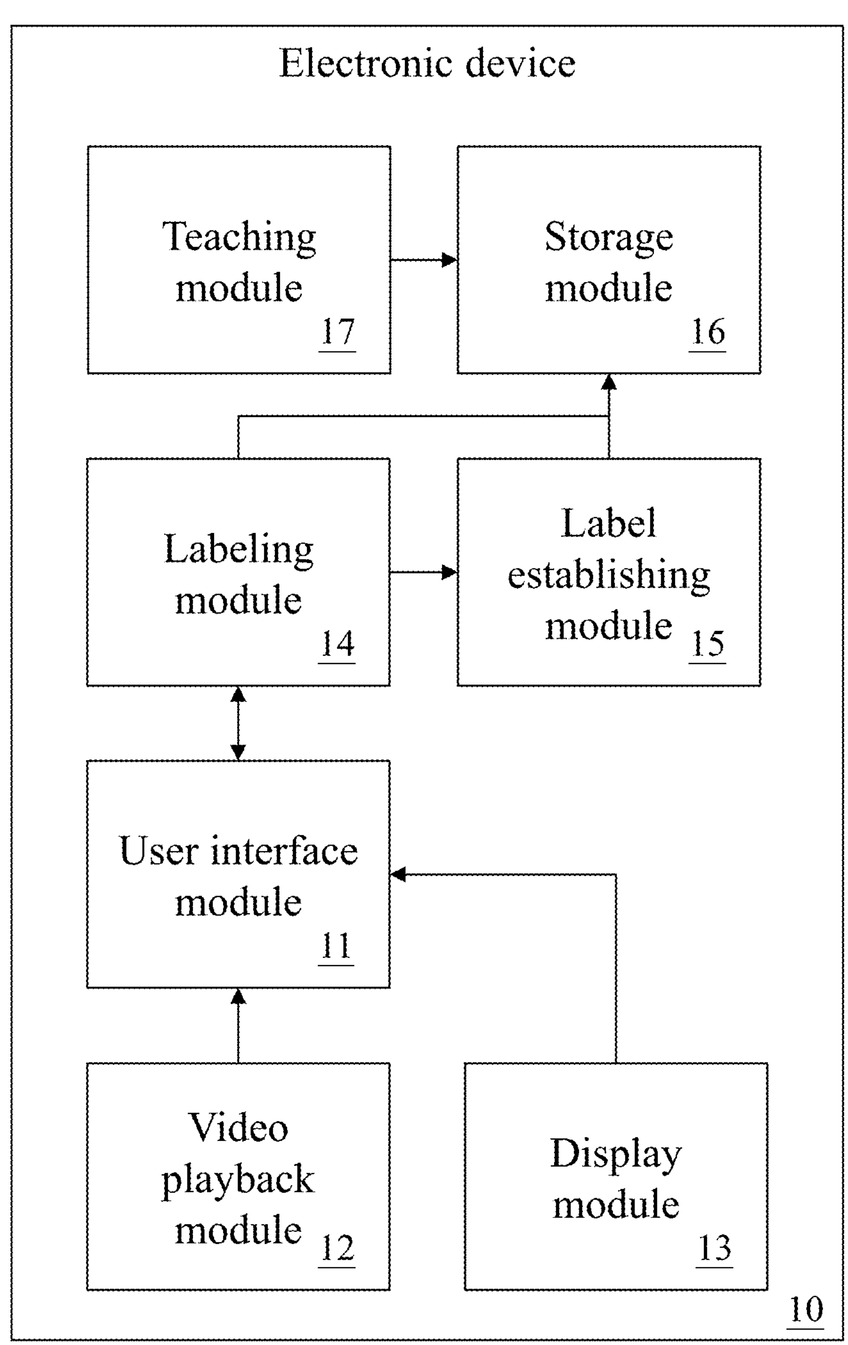
FIG. 1 is a block diagram of a surgical procedure labeling and teaching system of the present invention.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

The surgical procedure labeling and teaching system of the present invention will be described in the following paragraphs. Please refer to FIG. 1, which is a block diagram of a surgical procedure labeling and teaching system of the present invention.

The surgical procedure labeling and teaching system of the present invention is executed in an electronic device 10, the electronic device 10 includes a hardware processor is configured to execute following program modules stored in a memory: a user interface module 11, a video playback module 12, a display module 13, a labeling module 14, a label establishing module 15, a storage module 16 and a teaching module 17.

Figure 2:
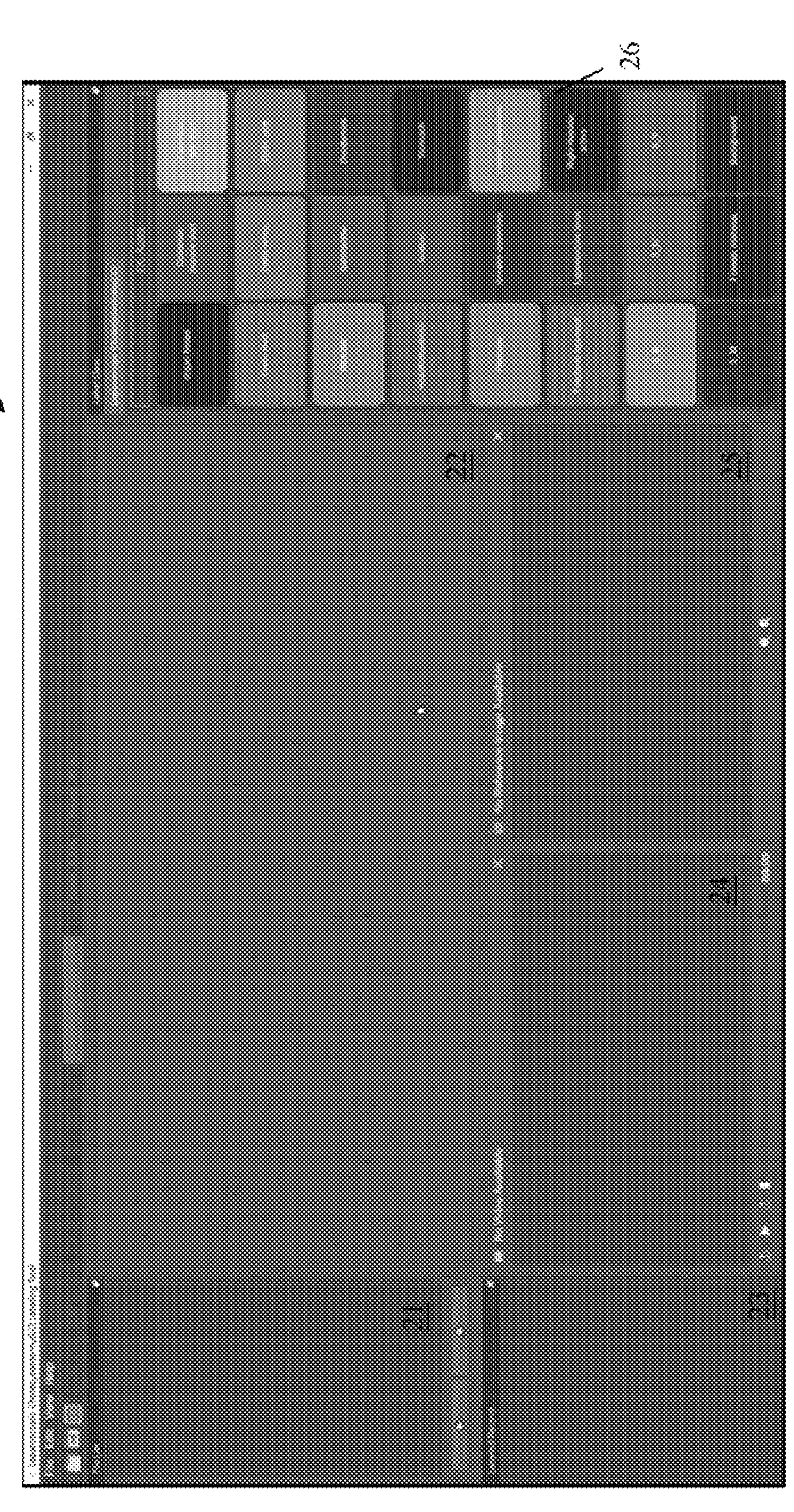
FIG. 2 is a schematic view of an initial user interface of a surgical procedure labeling and teaching system, according to the present invention.

The user interface module 11 is configured to display a user interface 20 including a surgical image selection area 21, a surgical image labeling area 22, a label record area 23, a surgery video playback area 24, an image-labeling reference area 25 and a surgery label selection area 26. Please refer to FIG. 2, which shows a schematic view of the user interface 20. FIG. 2 is a schematic view of an initial user interface of a surgical procedure labeling and teaching system, according to the present invention.

Figure 3:
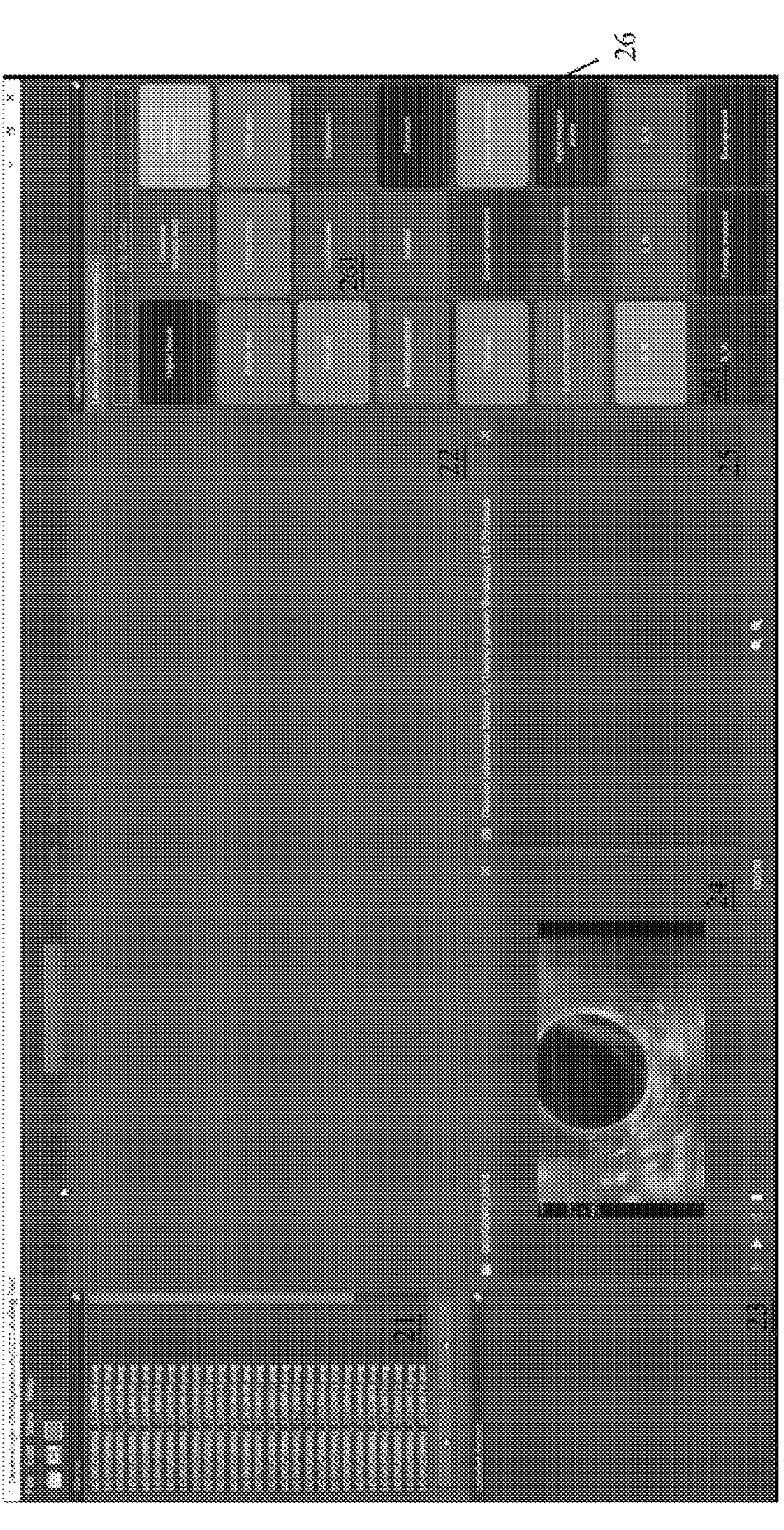
FIG. 3 is a schematic view of an area setting of a user interface of a surgical procedure labeling and teaching system, according to the present invention.

The surgical image selection area 21 is configured to obtain names of to-be-labeled surgical images stored in an assigned folder; in an embodiment, the to-be-labeled surgical images stored in the assigned folder correspond to a surgical procedure. In order to set the assigned folder, a user can drag and drop the assigned folder to the surgical image selection area 21, or the surgical image selection area 21 can be set with the assigned folder in the surgical procedure labeling and teaching system in advance; however, these examples are merely for exemplary illustration, and the application field of the present invention is not limited to these examples. The surgical image selection area 21 can display multiple names of the to-be-labeled surgical images through the display module 13, as shown in FIG. 3, which is a schematic view of an area setting of a user interface of the surgical procedure labeling and teaching system, according to the present invention. The names of to-be-labeled surgical images can include, for example, "LC-00258802_1238824.png", "LC-00258802_1240826.png", and "LC-00258802_1242828.png", and so on, as shown in FIG. 3; however, these examples are merely for exemplary illustration, and the application field of the present invention is not limited to these examples.

The surgery video playback area 24 is configured to obtain a surgery video stored in the assigned folder, and the surgery video also corresponds to the above-mentioned surgical procedure; the user can drag and drop the assigned folder to the surgery video playback area 24 to set the assigned folder, or the surgery video playback area 24 can be set with the assigned folder in the surgical procedure labeling and teaching system in advance; however, these examples are merely for exemplary illustration, and the application field of the present invention is not limited to these examples. The surgery video playback area 24 can play the surgery video through the video playback module 12, as shown in FIG. 3.

The image-labeling reference area 25 is configured to obtain and display one of the labeling-reference surgical images stored in the assigned folder, and the labeling-reference surgical image is an auxiliary reference image for comment illustration and simple labeling operation based on the to-be-labeled surgical image. The user can drag and drop the assigned folder to the image-labeling reference area 25 to set the assigned folder, or the image-labeling reference area 25 can be set with the assigned folder in the surgical procedure labeling and teaching system in advance; however, these examples are merely for exemplary illustration, and the application field of the present invention is not limited to these examples. The image-labeling reference area 25 can display the corresponding labeling-reference surgical image through the display module 13. It should be noted that the assigned folders assigned for the above-mentioned surgical image selection area 21, surgery video playback area 24 and image-labeling reference area 25 can be the same folder or different folders.

The surgery label selection area 26 is configured to display multiple surgery label blocks 261, as shown in FIGS. 2 and 3, the purposes pf the surgery label blocks 261 displayed on the surgery label selection area 26 will be illustrated in the following paragraphs. A name of the surgery label block 261 can be a name of human tissue (such as Lymphoid tissue), a name of organ (such as Gallbladder), or a name of surgical instrument (such as scalepel); however, these examples are merely for exemplary illustration, and the application field of the present invention is not limited to these examples.

Figure 4:
FIG. 4 is a schematic view showing an operation of selecting a name of to-be-labeled surgical image to change a user interface of a surgical procedure labeling and teaching system, according to the present invention.

Please refer to FIG. 4, which is a schematic view showing an operation of selecting a name of to-be-labeled surgical image to change the user interface of a surgical procedure labeling and teaching system, according to the present invention.

When one of the names of the to-be-labeled surgical images on the surgical image selection area 21 is selected, for example, in an embodiment, the name "LC-00258802_1238824.png" is selected, the to-be-labeled surgical image corresponding to the selected name "LC-00258802_1238824.png" is displayed on the surgical image labeling area 22 through the display module 13; at the same time, the labeling-reference surgical image corresponding to the selected name "LC-00258802_1238824.png" is displayed on the image-labeling reference area 25 through the display module 13. When one of the names of the to-be-labeled surgical images on the surgical image selection area 21 is selected, the label establishing module 15 establishes and displays a background label on the label record area 23.

Figure 5:
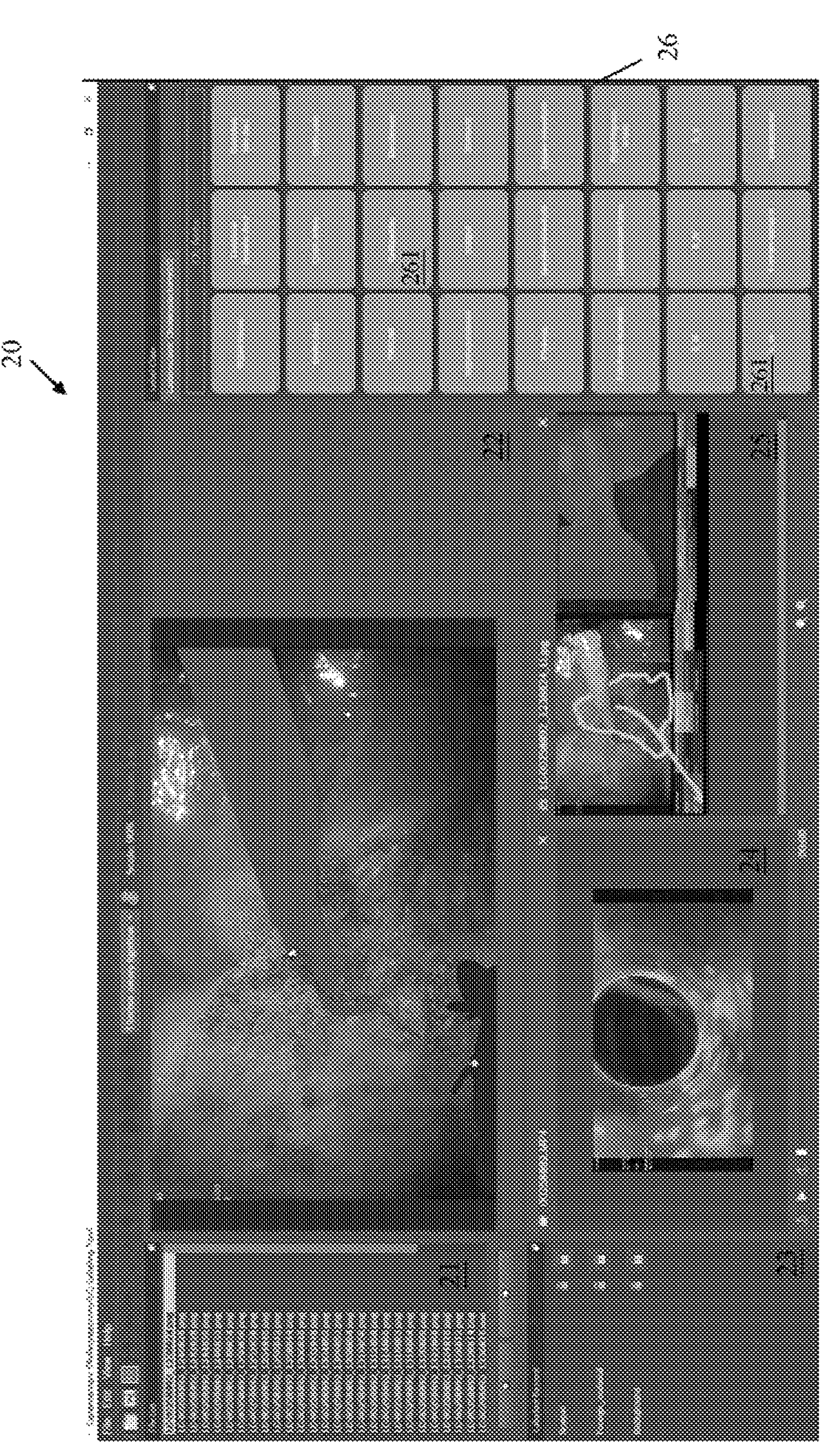
FIG. 5 is a schematic view showing a change in a user interface during a labeling process of a surgical procedure labeling and teaching system, according to the present invention.

Please refer to FIG. 5, which is a schematic view showing a change in a user interface during a labeling process of a surgical procedure labeling and teaching system, according to the present invention.

Figure 6:
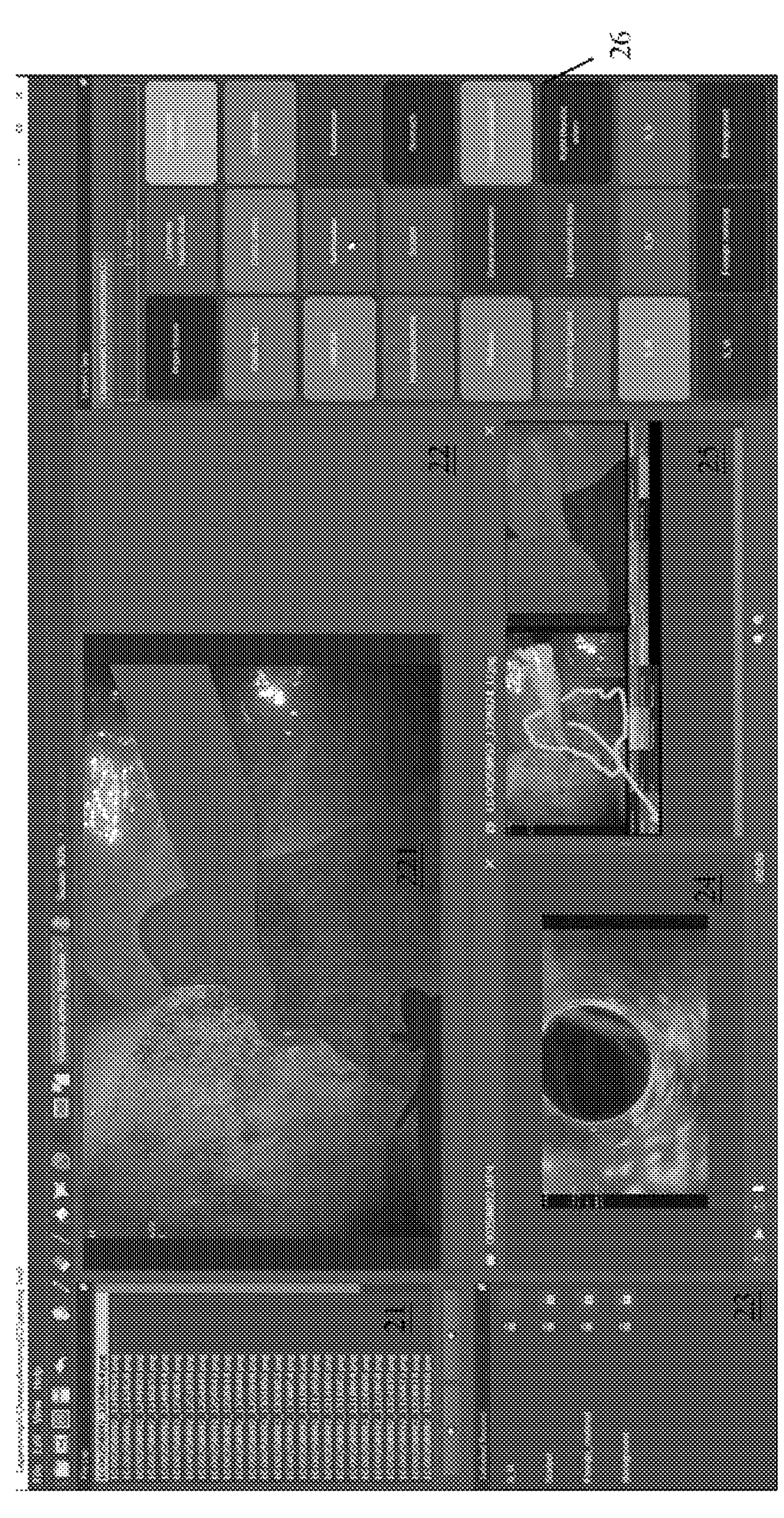
FIG. 6 is a schematic view of a change in a user interface to show a labeling result of a surgical procedure labeling and teaching system, according to the present invention.

In order to label the to-be-labeled surgical image displayed on the surgical image labeling area 22, a user can select one of the surgery label blocks 261 on the surgical image labeling area 26 and use the labeling model 14 to circle a surgery labeling area 221 on the surgical image labeling area 22. Circling the surgery labeling area 221 is to label a human tissue, an organ, or surgical instrument on the surgical image labeling area 22; the circling process on the surgical image labeling area 22 is shown by a dashed line in FIG. 5. When the circling process on the surgery labeling area 221 is completed, the surgery labeling area 221 is fully filled with a color corresponding to the selected surgery label block 261 on the surgical image labeling area 22, as shown in FIG. 6, which is a schematic view of a change in the user interface to show a labeling result, according to the surgical procedure labeling and teaching system of the present invention. The displaying effect shown in FIG. 6 is that the surgery labeling area 221 is fully filled color; however, the example is merely schematic, the application field of the present invention is not limited to the example.

It should be noted that, after the labeling module 14 selects the surgery label block 261 on the surgical image labeling area 26, all of the surgery label blocks 261 on the surgery label selection area 26 are not permitted to select, and all of the surgery label blocks are changed to display with the same effect, for example, in FIG. 5, the surgery label blocks 261 are displayed with grayscale effect, but it is merely for exemplary illustration, and the application field of the present invention is not limited to these examples.

After the surgery labeling area 221 on the surgical image labeling area 22 is circled, the label establishing module 15 establishes the name label on the label record area 23 based on the name corresponding to the selected surgery label block 261; in an embodiment, the name is "S_VI".

The user can continuously operate the labeling module 14 to select one of the surgery label blocks 261 on surgery label selection area and circle the corresponding surgery labeling area 221 on the surgical image labeling area 22, so as to complete the operation of circling the to-be-labeled surgical image. Please refer to FIG. 7, which is a schematic view of a labeling result of the to-be-labeled surgical image, according to the surgical procedure labeling and teaching system of the present invention.

Figure 7:
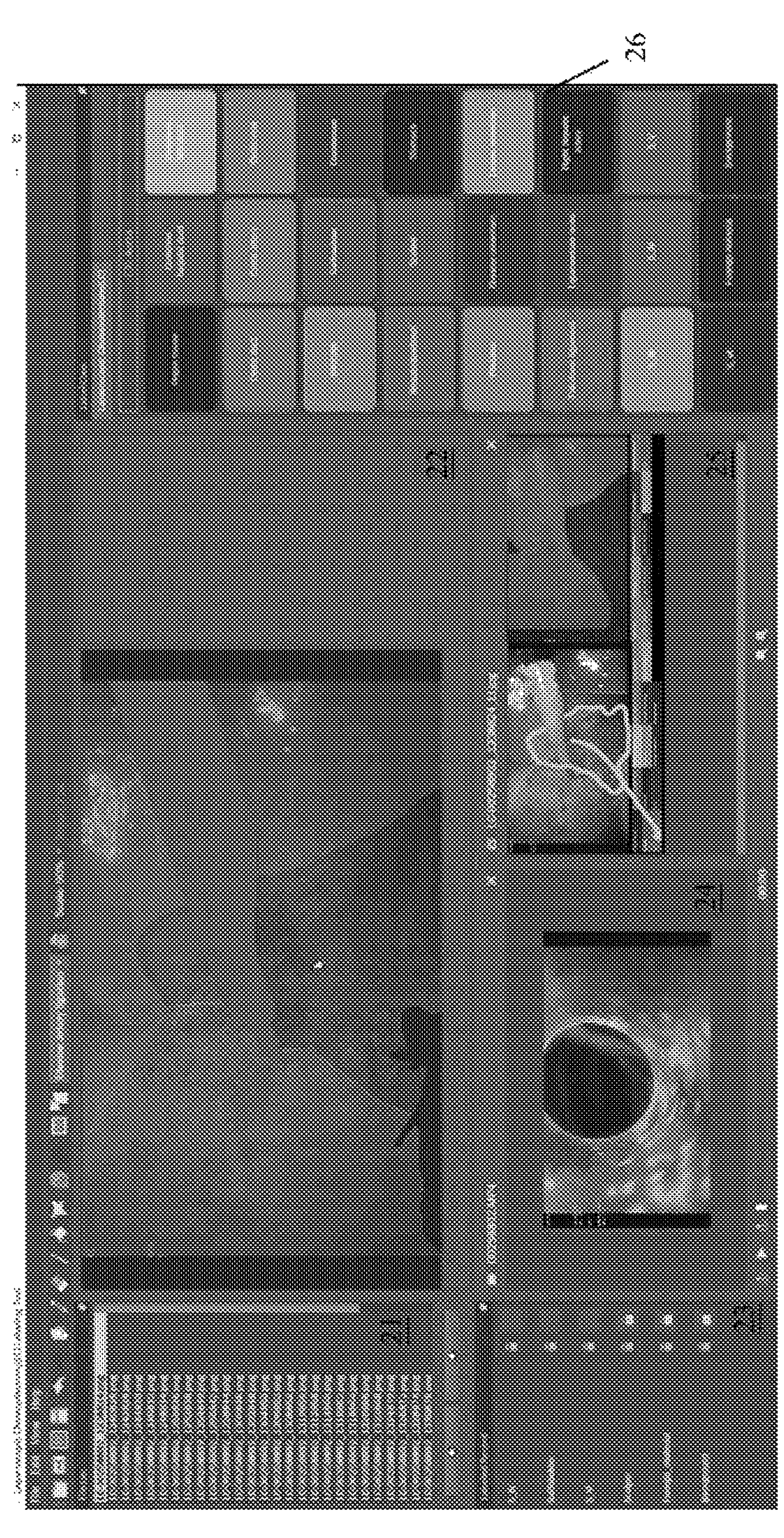
FIG. 7 is a schematic view of a labeling result of a to-be-labeled surgical image, according to surgical procedure labeling and teaching system of the present invention.

It should be noted that the surgery label blocks 261 displayed on the surgery label selection area 26 have different display priorities; on the surgical image labeling area 22, the surgery labeling area fully filled with the surgery label block having high display priority is always displayed over the surgery labeling area filled with the surgery label block having the low display priority, as shown in FIG. 7, the display priority of the surgery label block "scalpel" is higher than the display priorities of the surgery label blocks "S_VI", "Gallbladder" and "S_IV", the display priority of the surgery label block "foreign material" is higher than the display priorities of the surgery label blocks "S_VI" and "Gallbladder", the display priority of the surgery label block "S_VI" is higher than the display priorities of the surgery label blocks "Gallbladder" and "S_IV", and the display priority of the surgery label block "Gallbladder" is higher than the display priority of the surgery label block "S_IV".

After the operation of circling the surgery labeling areas on the to-be-labeled surgical image is completed, the storage module 16 can store the surgical image, which is labeled completely, as a labeled surgical image. For example, the labeled surgical image can include multiple surgery labeling areas filled with colors, and the labeled surgical image can be used for surgical procedure teaching.

Figure 8:
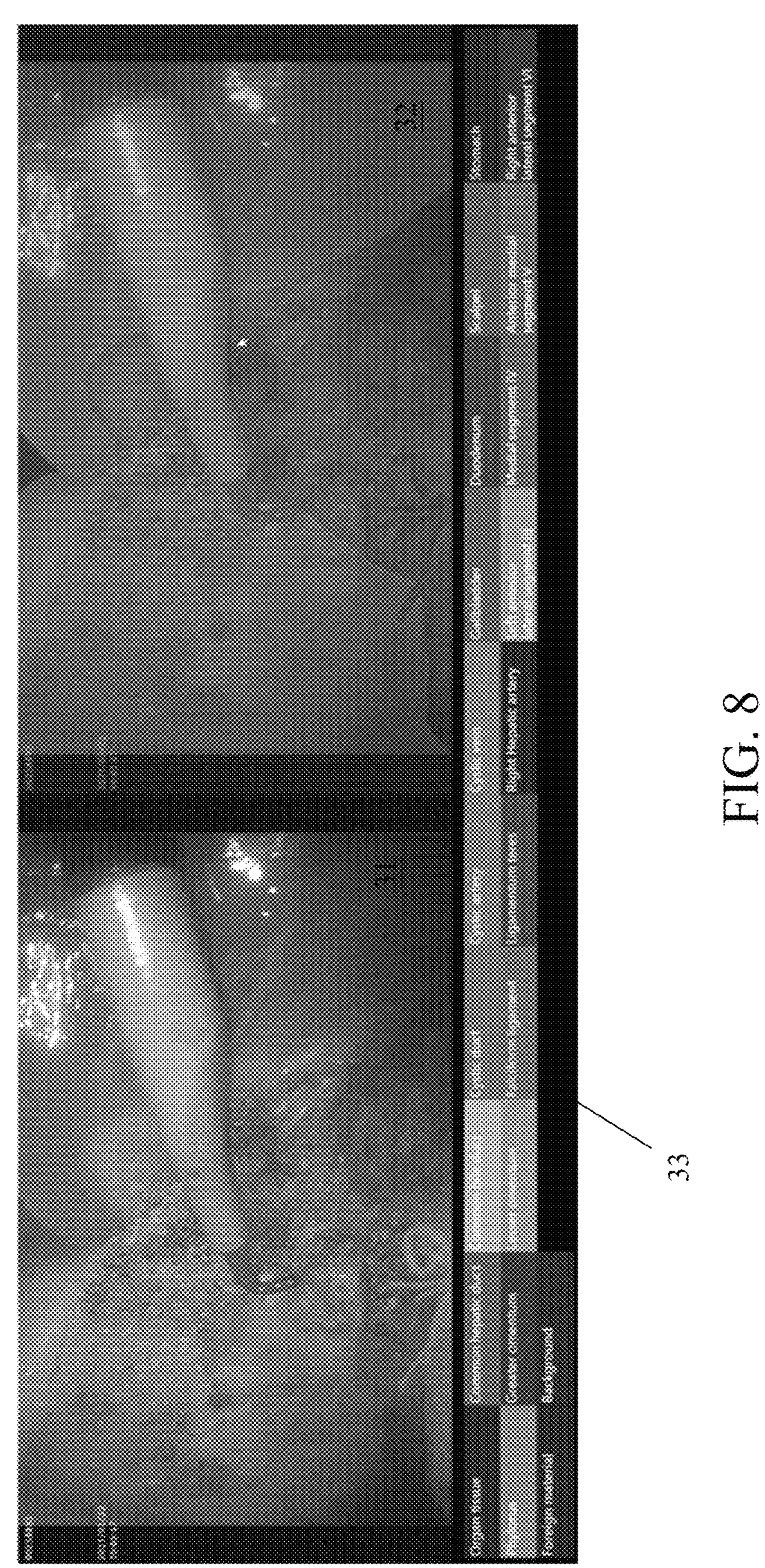
FIG. 8 is a schematic view of a teaching interface of a surgical procedure labeling and teaching system of the present invention.

In order to perform surgical procedure teaching, the teaching module 17 displays a teaching interface 30 including a to-be-labeled surgical image area 31, a labeled surgical image area 32 and a surgery label display area 33. Please refer to FIG. 8, which is a schematic view of a teaching interface of a surgical procedure labeling and teaching system, according to the present invention. The to-be-labeled surgical image is displayed on the to-be-labeled surgical image area 31, the labeled surgical image is displayed on the labeled surgical image area 32. Displaying the surgery labeling areas filled with colors of the labeled surgical image mapped to the to-be-labeled surgical image, and an auxiliary content corresponding to the surgery labeling area on the surgery label display area 33 can provide a surgical procedure teaching corresponding to the to-be-labeled surgical image.

Figure 9:
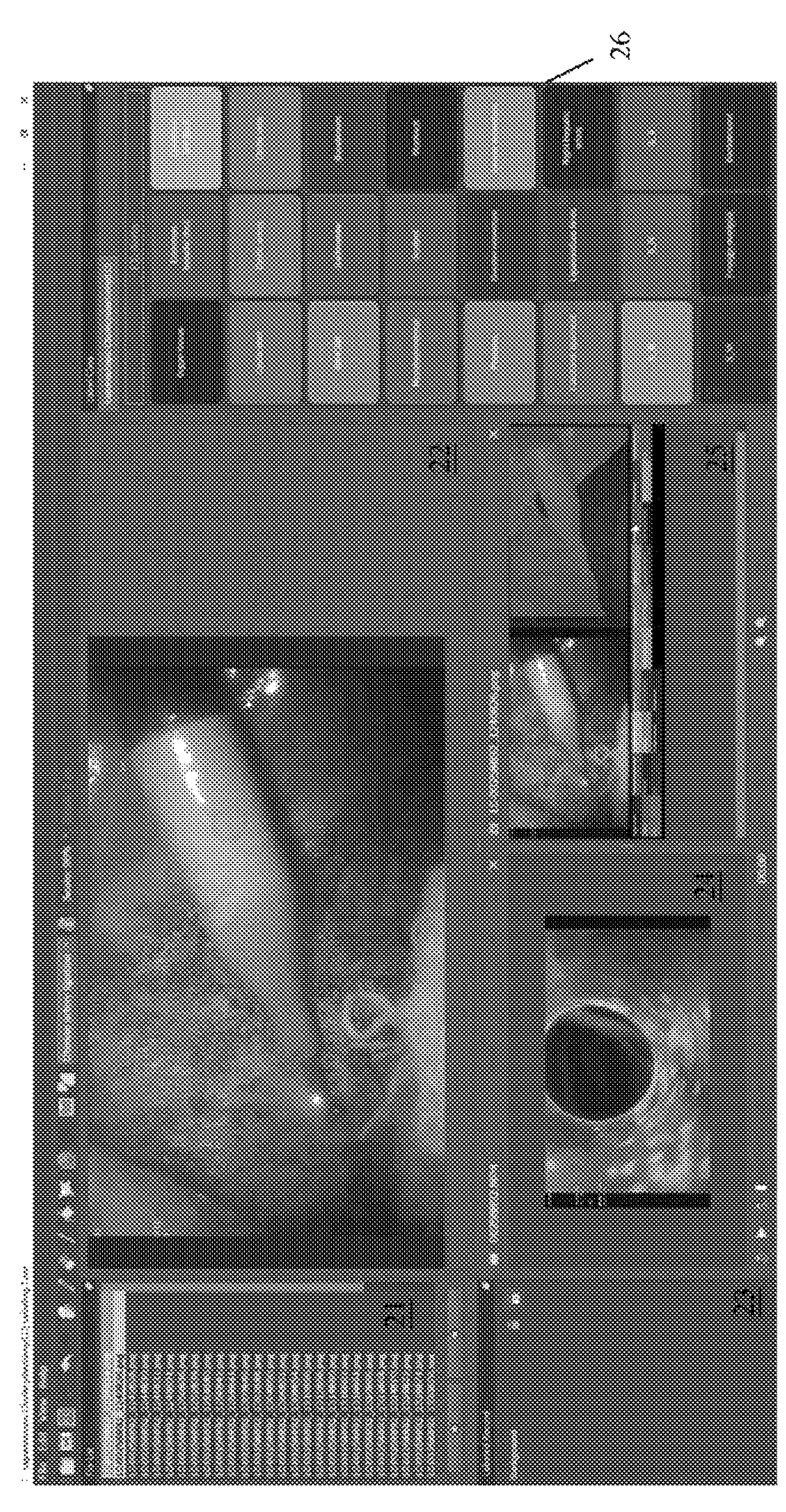
FIG. 9 is a schematic view of a displaying effect on a surgical image selection area, according to a surgical procedure labeling and teaching system of the present invention.

Please refer to FIG. 9, which is a schematic view of a displaying effect on a surgical image selection area, according to the surgical procedure labeling and teaching system of the present invention.

When one of the names of the to-be-labeled surgical images on the surgical image selection area 21 is selected, for example, in this embodiment, the name "LC-00258802_1240826.png" is selected, the to-be-labeled surgical image corresponding to the selected name "LC-00258802_1240826.png" is displayed on the surgical image labeling area 22 through the display module 13; at the same time, the labeling-reference surgical image corresponding to the selected name "LC-00258802_1240826.png" is displayed on the image-labeling reference area 25 through the display module 13. When one of the names of the to-be-labeled surgical images on the surgical image selection area 21 is selected, the label establishing module 15 establishes and displays the background label on the label record area 23.

Among the to-be-labeled surgical images, the name of the surgical image labeled already, the name of the surgical image being labeled, and the name of the surgical image not labeled yet are displayed with different background patterns on the surgical image selection area 21; for example, as shown in FIG. 9, the image name "LC-00258802_1238824.png" displayed with a background pattern of deeper grayscale background is the surgical image labeled already, the image name "LC-00258802_1240826.png" displayed with a background pattern of shallower grayscale background is the surgical image being-labeled, and the image names "LC-00258802_1242828.png" and "LC-00258802_1244830.png" displayed with no background pattern are the surgical images not labelled yet; however, these examples are merely for exemplary illustration, and the application field of the present invention is not limited to these examples.

When one of the names of to-be-labeled surgical images on the surgical image selection area 21 is selected, the video playback module 12 captures a part the surgery video in a period, which is from a video time point minus a preset time length to the video time point plus the preset time length, as a surgery video. The video time point is a video time point of the selected to-be-labeled surgical image. The video playback module 12 then plays the captured surgery video.

Particularly, in a condition that the video time point of the selected to-be-labeled surgical image is "00:30" and the preset time length is "10 seconds", when the name of the to-be-labeled surgical image is selected on the surgical image labeling area, the video playback module 12 captures a part of the video before and after the video time point "00:30" by "10 seconds" (that is, a time range from "00:20" to "00:40") as the captured surgery video, and plays the captured surgery video.

The operation of a method of the present invention will be illustrated in the following paragraphs. Please refer to FIGS. 10A and 10B, which are flowcharts of a surgical procedure labeling and teaching method of the present invention.

Figure 10A:
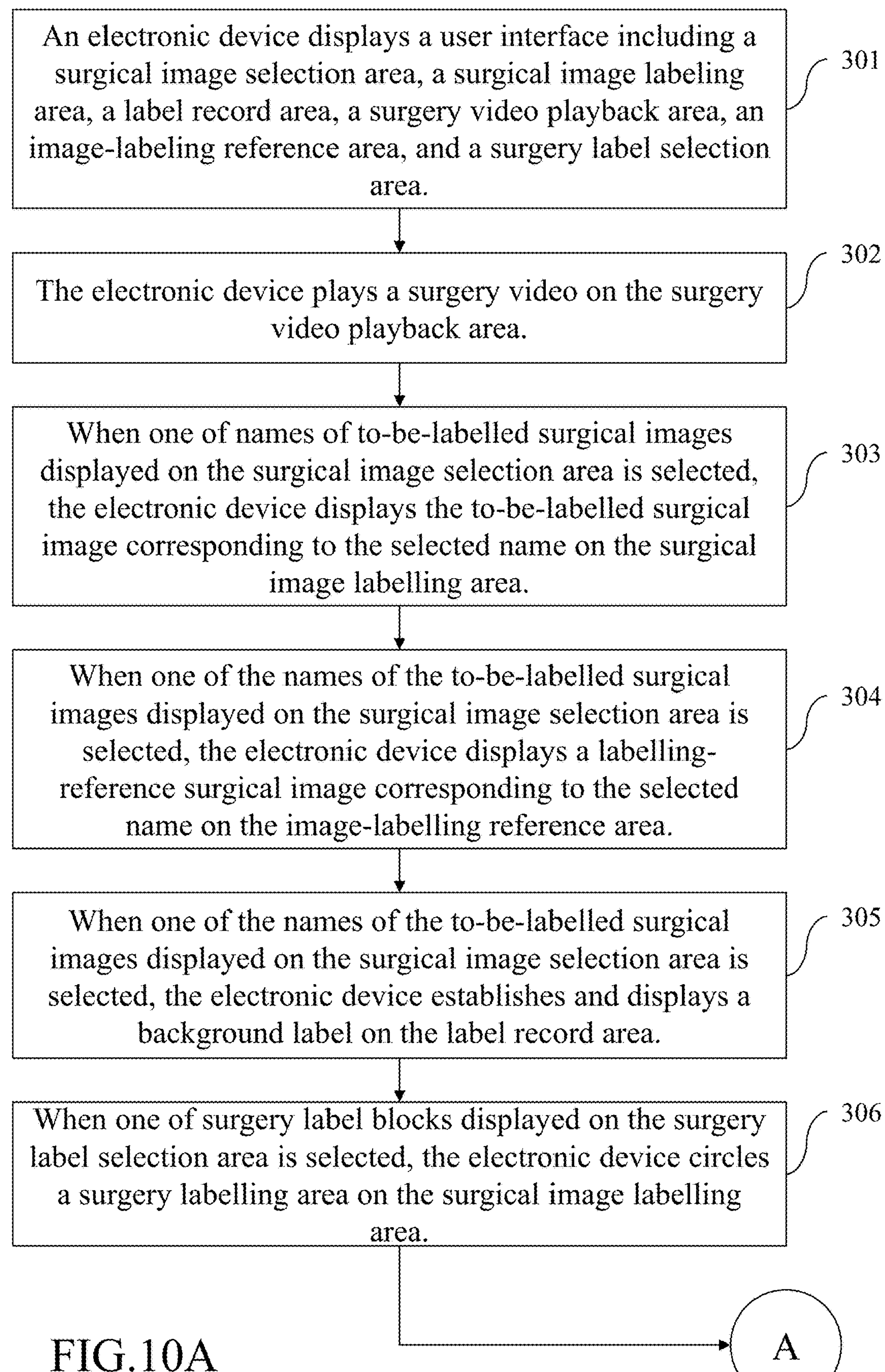

As shown in FIGS. 10A and 10B, the surgical procedure labeling and teaching method of the present invention includes the following steps. In a step 301, an electronic device displays a user interface including a surgical image selection area, a surgical image labeling area, a label record area, a surgery video playback area, an image-labeling reference area, and a surgery label selection area. In a step 302, the electronic device plays a surgery video on the surgery video playback area. In a step 303, when one of names of to-be-labelled surgical images displayed on the surgical image selection area is selected, the electronic device displays a to-be-labelled surgical image corresponding to the selected name on the surgical image labelling area. In a step 304, when one of the names of the to-be-labelled surgical images displayed on the surgical image selection area is selected, the electronic device displays a labelling-reference surgical image corresponding to the selected name on the image-labelling reference area. In a step 305, when one of the names of the to-be-labelled surgical images displayed on the surgical image selection area is selected, the electronic device establishes and displays a background label on the label record area. In a step 306, when one of surgery label blocks displayed on the surgery label selection area is selected, the electronic device receives multiple connected operating points in the surgical image labelling area to generate a surgery labelling area which is surrounded by multiple connected operating points. In a step 307, the electronic device fills the surgery labeling area with a color corresponding to the selected surgery label block on the surgical image labeling area, and establishes a name label based on a name corresponding to the selected surgery label block on the label record area. In a step 308, the electronic device stores the to-be-labelled surgical image, which is labeled already, as a labelled surgical image, wherein the labelled surgical image comprises surgery labeling areas filled with colors. In a step 309, the electronic device displays a teaching interface comprising a to-be-labeled surgical image area, a labelled surgical image area and a surgery label display area. In a step 310, the electronic device displays the to-be-labelled surgical image on the to-be-labelled surgical image area, and displays the labelled surgical image on the labelled surgical image area. In a step 311, the electronic device displays the surgery labelling areas of the labelled surgical image filled with colors and mapped to the to-be-labelled surgical image, and displays multiple auxiliary content blocks with colors and names corresponding to the surgery labelling areas on the surgery label display area, so as to provide a surgical procedure teaching corresponding to the to-be-labeled surgical image.

According to above-mentioned contents, the difference between the present invention and the conventional technology is that, in the present invention, when one of the names of to-be-labeled surgical images on the surgical image selection area of the user interface is selected, the to-be-labeled surgical image corresponding to the selected name is displayed on the surgical image labeling area of the user interface, and after one of the surgery label blocks on the surgery label selection area of the user interface is selected, the user can circle the surgery labeling area to establish the surgery feature label on the surgical image labeling area, and the teaching interface can map the labeled surgical image to the to-be-labeled surgical image, so as to provide the surgical procedure teaching corresponding to the to-be-labeled surgical image. Therefore, the above-mentioned technical solution of the present invention is able to solve the conventional technology problem of lacking an auxiliary tool to label the surgical procedure video for better medical teaching, so as to achieve the technical effect of providing surgical procedure teaching by using the labeling-reference surgical image to assist the labeling and selecting of the to-be-labeled surgical image.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A surgical procedure labeling and teaching system, executed in an electronic device, the electronic device includes a hardware processor is configured to execute following instructions stored in a memory:

displaying a user interface, wherein the user interface comprises a surgical image selection area, a surgical image labeling area, a label record area, a surgery video playback area, an image-labeling reference area and a surgery label selection area;

playing a surgery video on the surgery video playback area;

when one of names of to-be-labelled surgical images on the surgical image selection area is selected, displaying a to-be-labelled surgical image corresponding to the selected name on the surgical image labelling area, and displaying a labelling-reference surgical image corresponding to the selected name on the image-labelling reference area;

when one of names of to-be-labelled surgical images on the surgical image selection area is selected, calculating a period from a video time point minus a preset time length to the video time point plus the preset time length based on the video time point of the selected to-be-labeled surgical image, and capturing a part of the surgery video in the period to generate and play a captured surgery video;

when one of surgery label blocks on the surgery label selection area is selected, receiving multiple connected operating points in the surgical image labelling area to generate a newly added surgery labelling area wherein an edge of the newly added surgery labelling area is formed by the multiple connected operating points, and filling the surgery labeling area with a color corresponding to the selected surgery label block on the surgical image labeling area, wherein all of the surgery label blocks on the surgery label selection area are not permitted to select until the newly added surgery labelling area is generated;

when coordinates of at least one of the operating points are located within a coordinate range of a previously labelled surgery labelling area, a display priority of the newly added surgery labelling area or the previously labelled surgery labelling area which is labelled as surgical instrument or foreign material is higher than the display priority of the newly added surgery labelling area or the previously labelled surgery labelling area which is labelled as organs, the newly added surgery labelling area or the previously labelled surgery labelling area having a high display priority is displayed over the newly added surgery labelling area or the previously labelled surgery labelling area having a low display priority;

establishing and displaying a background label on the label record area, wherein after the newly added surgery labelling area is generated on the surgical image labelling area, establishing a name label on the label record area based on a name corresponding to the selected surgery label block;

storing the labelled to-be-labelled surgical image as a labelled surgical image, wherein the labelled surgical image comprises surgery labeling areas filled with colors; and displaying a teaching interface comprising a to-be-labeled surgical image area, a labelled surgical image area and a surgery label display area, wherein displaying the to-be-labelled surgical images on the to-be-labelled surgical image area, and displaying the labelled surgical image on the labelled surgical image area, and providing a surgical procedure teaching corresponding to the to-be-labeled surgical image by surgery labelling areas of the labelled surgical image filled with colors and mapped to the to-be-labelled surgical image, and displaying multiple auxiliary content blocks with colors and names corresponding to the surgery labelling areas on the surgery label display area.

2. The surgical procedure labelling and teaching system according to claim 1, wherein displaying the name of the surgical image labelled already, the name of the surgical image being labeled, and the name of surgical image not labelled yet, with different background patterns on the surgical image selection area.

3. The surgical procedure labelling and teaching system according to claim 1, wherein when one of the surgery label blocks displayed on the surgery label selection area is selected, all of the surgery label blocks on the surgery label selection area are not permitted to select, and all of the surgery label blocks are displayed with the same effect.

4. A surgical procedure labelling and teaching method, comprising:

displaying a user interface comprising a surgical image selection area, a surgical image labeling area, a label record area, a surgery video playback area, an image-labeling reference area, and a surgery label selection area, by an electronic device;

playing a surgery video on the surgery video playback area, by the electronic device;

when one of names of to-be-labelled surgical images displayed on the surgical image selection area is selected, displaying a to-be-labelled surgical image corresponding to the selected name on the surgical image labelling area, by the electronic device;

when one of the names of the to-be-labelled surgical images displayed on the surgical image selection area is selected, displaying a labelling-reference surgical image corresponding to the selected name on the image-labelling reference area, by the electronic device;

when one of names of to-be-labelled surgical images on the surgical image selection area is selected, calculating a period from a video time point minus a preset time length to the video time point plus the preset time length based on the video time point of the selected to-be-labeled surgical image, and capturing a part of the surgery video in the period to generate and play a captured surgery video, by the electronic device;

establishing and displaying a background label on the label record area, by the electronic device;

when one of surgery label blocks displayed on the surgery label selection area is selected, receiving multiple connected operating points in the surgical image labelling area to generate a newly added surgery labelling area by the electronic device wherein an edge of the newly added surgery labelling area is formed by the multiple connected operating points, wherein all of the surgery label blocks on the surgery label selection area are not permitted to select until the newly added surgery labelling area is generated;

when coordinates of at least one of the operating points are located within a coordinate range of a previously labelled surgery labelling area, a display priority of the newly added surgery labelling area or the previously labelled surgery labelling area which is labelled as surgical instrument or foreign material is higher than the display priority of the newly added surgery labelling area or the previously labelled surgery labelling area which is labelled as organs, the newly added surgery labelling area or a previously labelled surgery labelling area having a high display priority is displayed over the newly added surgery labelling area or a previously labelled surgery labelling area having a low display priority;

filling the surgery labeling area with a color corresponding to the selected surgery label block on the surgical image labeling area, and establishing a name label based on a name corresponding to the selected surgery label block on the label record area, by the electronic device;

storing the to-be-labelled surgical image, which is labeled already, as a labelled surgical image, by the electronic device, wherein the labelled surgical image comprises surgery labeling areas filled with colors;

displaying a teaching interface comprising a to-be-labeled surgical image area, a labelled surgical image area and a surgery label display area, by the electronic device;

displaying the to-be-labelled surgical image on the to-be-labelled surgical image area, and displaying the labelled surgical image on the labelled surgical image area, by the electronic device; and displaying surgery labelling areas of the labelled surgical image filled with colors and mapped to the to-be-labelled surgical image, and displaying multiple auxiliary content blocks with colors and names corresponding to the surgery labelling areas on the surgery label display area, by the electronic device, so as to provide a surgical procedure teaching corresponding to the to-be-labeled surgical image.

5. The surgical procedure labelling and teaching method according to claim 4, further comprising:

displaying the name of the surgical image labelled already, the name of the surgical image being labeled, and the name of surgical image not labelled yet, with different background patterns on the surgical image selection area, by the electronic device.

6. The surgical procedure labelling and teaching method according to claim 4, wherein when one of the surgery label blocks displayed on the surgery label selection area is selected by the electronic device, all of the surgery label blocks on the surgery label selection area are not permitted to select, and all of the surgery label blocks are displayed with the same effect.

* * * * *